United States Patent

Upton et al.

[11] Patent Number: 6,141,037
[45] Date of Patent: Oct. 31, 2000

[54] VIDEO CAMERA SYSTEM AND RELATED METHOD

[75] Inventors: Wayne Upton; Robert Walls, both of Santa Barbara, Calif.

[73] Assignee: Linvatec Corporation, Largo, Fla.

[21] Appl. No.: 09/044,090

[22] Filed: Mar. 18, 1998

[51] Int. Cl.$^7$ .................................................. A62B 1/04
[52] U.S. Cl. ........................ 348/65; 348/69; 600/100; 128/908
[58] Field of Search ........................ 348/65–68, 43, 348/69, 70, 211; 600/100, 110, 421, 133, 112; 128/908; A62B 1/04

[56] References Cited

U.S. PATENT DOCUMENTS

| | | | |
|---|---|---|---|
| 4,170,997 | 10/1979 | Pinnow et al. | 600/108 |
| 4,349,014 | 9/1982 | Takamatsu | 348/43 |
| 4,633,304 | 12/1986 | Nagasaki | 348/43 |
| 4,677,471 | 6/1987 | Takamura et al. | 600/133 |
| 4,831,456 | 5/1989 | Takamura | 348/374 |
| 4,846,571 | 7/1989 | Jelalian et al. | 356/5 |
| 4,878,485 | 11/1989 | Adair | 600/133 |
| 4,895,138 | 1/1990 | Yabe | 600/110 |
| 4,918,521 | 4/1990 | Yabe et al. | |
| 4,931,867 | 6/1990 | Kikuchi . | |
| 4,975,926 | 12/1990 | Knapp . | |
| 4,977,418 | 12/1990 | Canty | 348/82 |
| 4,977,618 | 12/1990 | Allen . | |
| 5,027,433 | 6/1991 | Menadier et al. . | |
| 5,089,895 | 2/1992 | Fraker et al. | 348/374 |
| 5,231,393 | 7/1993 | Strickland | 340/936 |
| 5,257,100 | 10/1993 | Hattori et al. | 348/65 |
| 5,428,386 | 6/1995 | D'Alfonso et al. . | |
| 5,536,244 | 7/1996 | Müeller et al. | 600/133 |
| 5,587,736 | 12/1996 | Walls | 348/65 |
| 5,696,553 | 12/1997 | D'Alfonso et al. | 348/211 |
| 5,841,491 | 11/1998 | D'Alfonso et al. | 348/65 |
| 5,868,664 | 2/1999 | Speier et al. | 600/112 |
| 5,882,305 | 3/1999 | Dumoulin et al. | 600/421 |
| 6,073,569 | 6/2000 | Motsenbocker et al. | 144/61.1 |

Primary Examiner—Chris S. Kelley
Assistant Examiner—Tung Vo
Attorney, Agent, or Firm—Howrey Simon Arnold & White, LLP

[57] ABSTRACT

A video camera system is provided in which the camera head is powered at least in part by electrical energy converted from optical energy provided by a light source. In one implementation, communication between the camera head and control circuitry thereof occurs by means of a wireless communications interface.

30 Claims, 5 Drawing Sheets

VIDEO CAMERA SYSTEM AND RELATED METHOD

I. BACKGROUND OF THE INVENTION

The field of this invention relates generally to video cameras and systems, and more specifically, to a video camera system in which the camera head thereof is powered at least in part by electrical energy converted from optical energy produced by a light source.

In the recent past, the need for small, lightweight video cameras using a solid state image sensor ("imager") such as a charge coupled device ("CCD"), charge injection device ("CID"), or a metal oxide semiconductor ("MOS") device, has rapidly developed for both medical and industrial applications. One medical application involves a video camera attached to an endoscope to allow observation of a surgical site, an internal body structure, or an organ. With a diameter of from 4 to 10 mm., endoscopes are passed into body cavities through small holes to observe structures and perform procedures previously requiring large surgical openings.

In this arrangement, the imager may be contained in a small camera head and attached to the endoscope eyepiece so that the camera head/endoscope combination, or videoendoscope, is lightweight and easily manipulable by a surgeon. A flexible cable connects the camera head to the rest of the camera electronics which are usually included in a camera control unit located remotely from the camera head, and connected via a cable. The camera control unit includes control and video processing circuitry which sends operating signals to the imager and receives signals from the imager which are processed for video display. The camera control unit is also coupled to a video monitor for viewing of the surgical site by one or more physicians. The smallest cameras are made with a single imager but other multiple-imager cameras are also in use, as described in U.S. Pat. No. 5,428,386, which is hereby fully incorporated by reference herein as though set forth in full.

An industrial application employing an imager involves observation of industrial processes in which direct observation by a person is unsafe or otherwise impractical. Such processes include those occurring in nuclear power generating stations, furnaces or engine compartments, or other processes which are generally inaccessible. Here, a camera head including an imager may be attached to a hole in the wall of the vessel in which the process occurs. The camera head is then connected by cable to a camera control unit and video monitor at a remote location in similar fashion to that described above.

Additional background and details regarding video cameras, and their use in medical endoscopic applications, are provided in the following co-pending applications and/or patents, each of which is assigned to Linvatec Corp., and each of which is hereby incorporated by reference herein as though set forth in full:

| Serial/U.S. Pat No. | Filing/Issue Date | Title |
| --- | --- | --- |
| USPN 5,696,553 | Issued December 9, 1997 | REMOTE IMAGER VIDEO CAMERA CABLE COMPENSATION CIRCUITRY |
| USSN 08/687,086 | Filed July 23, 1996 | FIBERSCOPE ENHANCEMENT SYSTEM |
| USSN 08/589,875 | Filed January 23, 1996 | REMOTE CCD VIDEO CAMERA WITH NON-VOLATILE DIGITAL MEMORY |
| USPN 5,587,736 | Issued December 24, 1996 | STERILIZABLE CCD VIDEO CAMERA |
| USSN 08/606,220 | Filed February 23, 1996 | ELECTRICALLY-ISOLATED STERILIZABLE, ENDOSCOPIC VIDEO CAMERA HEAD |
| USPN 5,428,386 | Issued June 27, 1995 | REMOTE 3D VIDEO CAMERA SYSTEM |

A critical design goal of an endoscopic CCD video camera is electrical safety, both from the standpoint of the operator, and from the standpoint of the patient. Of particular relevance in this regard is the recently adopted safety requirements and regulations of the unified European Community (EC)—the International Electrotechnical Commission, Medical Equipment Particular Standards for Safety of Endoscopic Equipment (IEC 601-2-18)—which are not only becoming common for all Europe, but are finding acceptance world-wide, including within testing agencies in the United States such as the Underwriters Laboratories (UL) standard UL2601. One specific aspect of these safety regulations states that endoscopic equipment that contacts the patient, and in some cases the operator, must be electrically isolated from ground and power sources.

A problem thus arises because most endoscopic video cameras include a grounded metal housing to (1) protect the sensitive CCD imager and associated electronics from susceptibility to externally generated electromagnetic interference (EMI) and (2) control emissions of electro-magnetic energy generated internally by the camera head circuitry. The need to achieve acceptable electromagnetic compatibility (EMC), that is, to control electromagnetic susceptibility and emissions, is quite important. This is especially true in the surgical setting in which there often exists both strong sources of EMI such as electrocautery units and sensitive instruments such as oxygen and $CO_2$ monitors.

Moreover, permissible electromagnetic emission levels are now specified by domestic and international regulations in the same way as other safety standards. In Europe, pursuant to International Electrotechnical Commission IEC 601-1-2, the governing standards are defined by CISPR 11, IEC 801-2, IEC 801-3, IEC 801-4, and IEC 801-5; in the United States, the Food and Drug Administration (FDA) has set forth the applicable standard in MDS 201-0004; and in the United European community (EU), according to an EMC Directive, the governing standards are essentially a composite of the above. In current endoscopic video cameras, the metal housing can easily contact the patient or operator, thus interfering with the objective of achieving compliance with applicable domestic and international safety standards.

Another problem is the difficulty of isolating the patient or user from the power sources (typically located in the control unit) used to drive the imager electronics and the camera control unit. Attempts to isolate the camera head from the endoscope by constructing the endoscope eyepiece from a non-metallic material have not proven entirely successful because the limited isolation provided thereby has been easily bridged by the operator's wet hand. Furthermore, there are currently no industry or agency standards that control the eyepiece to coupler attachment so that the amount of isolation at this interface is uncertain.

The problem is even worse in configurations employing one piece video-endoscopes in which the camera head and endoscope are screwed together or permanently joined. Such configurations have recently become more popular as physicians have become more comfortable with the practice of viewing images produced by an endoscope on a television monitor, in contrast to viewing these images directly through the endoscope eyepiece. Such a design eliminates the eyepiece, and with it any possible isolation available therefrom by creating a direct connection between the metal endoscope and the metal camera head housing.

Further, prior attempts to achieve electrical isolation have not proven successful. For example, Kikuchi, U.S. Pat. No. 4,931,867, describes an approach in which the camera control electronics are segregated into a camera input circuit and a camera output circuit which are isolated from one another through isolation circuitry. This approach is not satisfactory because it allows the camera input circuit and cable shield to float relative to the camera output circuit and video output. Consequently, the potential between this circuitry can become large and induce noise into the sensitive camera circuits. Moreover, electrical isolation between the patient and the metal enclosure of the camera head is not achieved.

Another critical design goal of an endoscopic CCD video camera is sterilizability. Because the camera head and cable are used within the sterile field (an arbitrary area around the surgical site) they must be disinfected like other surgical instruments. The steam autoclave method has long been the preferred method for sterilization, especially for instruments that can withstand the necessary high temperature, 134° C., and the extreme conditions associated with steam sterilization. In the past, instruments such as endoscopic cameras were not thought as being able to withstand the steam autoclave process. Accordingly, these instruments were either treated by less effective means such as cold soak processes or moderate temperature (55° C.) processes, or the camera head and cable were covered with a sterile disposable plastic cover during surgery. Each of these methods has significant disadvantages when compared with the steam autoclave method. For example, the cold soak processes do not achieve the same level of sterility, and the moderate temperature processes involve longer cycle times (2 hours) and the handling and disposal of highly toxic chemicals.

Recently, short exposure steam sterilization techniques have been developed to sterilize instruments more rapidly. One such method, known as flash sterilization, reduces the usual steam autoclave time of 45 minutes to less than 10 minutes by using vacuum evacuation of the steam chamber and elimination of the cloth wrapping procedure that protects the sterilized instruments during storage. The appearance of increasingly virulent contaminates and the need to quickly prepare instruments between procedures has made flash steam sterilization the method of choice for many surgical instruments.

The problem is that the camera cable and associated camera head connector are particularly vulnerable to damage from the foregoing cleaning and sterilization processes and historically have been the first to fail in use. Another problem is that the interruption in the integrity of the camera head which is incidental to the need to couple a cable to the camera head with a camera head connector interferes with the objective of providing a camera head which is sufficiently durable and sealed, that it is capable of undergoing the steam autoclave process while providing a waterproof environment to the interior camera head electronics.

A third design goal of a CCD video camera is that it be lightweight and easy for a surgeon to manipulate. The problem is that the camera head cable can be cumbersome and make it more difficult to manipulate the camera head. Although, as disclosed in U.S. Pat. No. 4,633,304, attempts have been made to eliminate the cable by establishing a wireless interface between an insertion section of an endoscope assembly and an operating unit, such efforts have not proven practical because these efforts have included the introduction of a relatively heavy and bulky local power supply such as a battery. A relatively heavy and bulky local power supply such as a battery is problematic because it does not permit easy manipulation of the video camera head, and is susceptible to damage during the steam autoclave sterilization process. Furthermore, the need to monitor and periodically recharge batteries, or interchange them with recharged units, resulting in periodic unsealing of the camera head, contributes to the undesirability of this approach.

A fourth design goal of a CCD video camera is avoiding or reducing interference between externally or internally generated radiation and the camera electronics. The problem is that, as mentioned earlier, a grounded metal housing is sometimes included for this purpose; however, it may interfere with achieving compliance with applicable safety standards. Moreover, the cable linking the camera head to the control unit is a major source of this interfering radiation, but substitution of a wireless communications interface for the cable may necessitate the introduction of a relatively heavy and bulky power supply.

A fifth design goal of a CCD video camera system is repairability. The problem is that the percentage of repairs that are related to cable failures is significant; however, again, the substitution of a wireless communications interface for the cable between the camera head and the control unit may necessitate the introduction of a relatively heavy and bulky power supply.

Consequently, it is an object of the subject invention to provide a video camera head configured for use in an endoscopic video camera system which permits substantial electrical isolation of the patient from power sources and ground. Another objective is to provide a video camera head which is readily sterilizable through the steam autoclave process. A third objective is to provide a video camera head which is lightweight and easy to manipulate. A fourth objective is to provide a wireless interface between the camera head and a corresponding control unit which avoids placement of a power supply within the camera head which is heavy, bulky, or requires periodic maintenance. Further objects of the invention include utilization of the above concepts alone or in combination. Additional advantages and objects will be set forth in the description which follows, or will be apparent to those of ordinary skill in the art who practice the invention.

II. SUMMARY OF THE INVENTION

To achieve the foregoing objects and advantages, and in accordance with the purpose of the invention as embodied and broadly described herein, there is provided: a video camera system comprising: control circuitry for processing an electronic image as produced by the imager; a camera head configured for placement along a first optical path; a light source; a second optical path extending from the light source to the camera head for transmitting optical energy from the light source; the camera head comprising: camera head electronics including an imager for producing an electronic image; and a power source for converting at least a portion of the optical energy as transmitted along the second optical path into electrical energy and using the same to power at least part of the camera head electronics.

Other aspects of the subject invention involve the foregoing in combination with an endoscope, or a wireless communications interface between the camera head and control circuitry for allowing wireless communication between the control circuitry and the camera head.

A related method involves the following steps: providing optical energy from a light source; converting the optical energy into electrical energy; providing camera electronics including an imager; powering at least a portion of the camera head electronics with the electrical energy; actuating the camera electronics to produce an electronic image; and processing the electronic image.

Another related method involves the following steps: providing optical energy from a light source; converting the optical energy into electrical energy; providing camera electronics including an imager; providing control circuitry; actuating the camera electronics to produce an electronic image; and passing the electronic image to the control circuitry through a wireless communications interface.

Another aspect of the subject invention involves practicing the foregoing methods in combination with an endoscope.

IV. DESCRIPTION OF THE PREFERRED EMBODIMENTS

Figure 1:
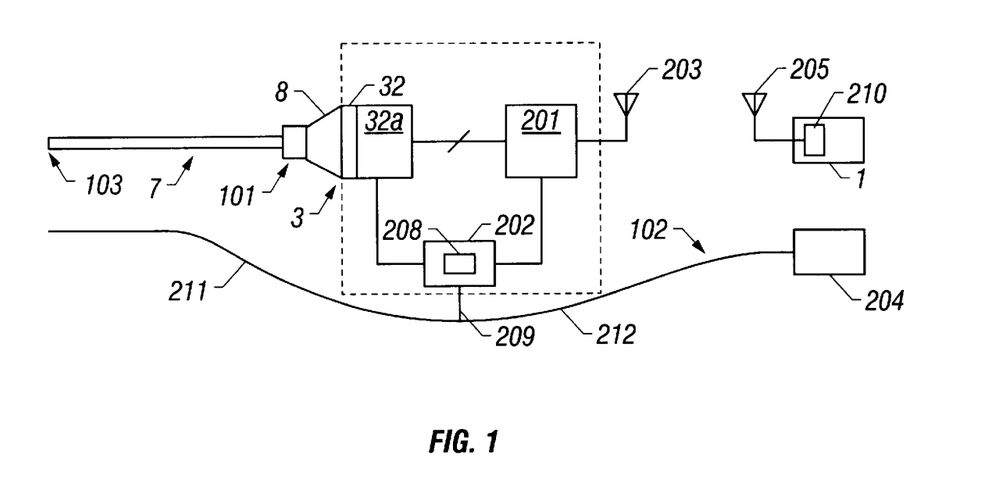
FIG. 1 is a block diagram of a system incorporating a first embodiment of the subject invention.

A block diagram of a preferred embodiment of the subject invention is illustrated in FIG. 1. As shown, camera head 3 is coupled via coupler 8 to endoscope 7.

Camera head 3 comprises imager 32 and related electronics 32a. This imager is advantageously a solid state imager such as a CCD. Also provided are transceiver 201, antenna 203, and local power source 202. The local power source 202 is used to power the imager 32, related electronics 32a, and the transceiver 201.

Preferably, imager 32 is an imager which has suitable low power characteristics, such as a CMOS imager, which typically requires only about 30 mW to operate, or a CCD imager which has similar low power characteristics to CMOS imagers. An advantage of a CMOS imager relative to a CCD imager is that a CMOS imager typically is made using the same silicon fabrication processes as most integrated circuits. That allows the imager electronics 32a to be built onto, and packaged with, the same piece of silicon as the imager. The result is that a one-chip video camera is possible, in which the imager and related electronics are integrated into a single chip.

The camera head 3 is configured to communicate with control unit 1 through a wireless interface. To that end, the control unit 1 is equipped with transceiver 210 and antenna 205.

Together, transceivers 201 and 210, and antennas 203 and 205, comprise a wireless interface. Advantageously, the wireless interface is bidirectional in order to accommodate the need to transmit control and synchronization information from the control unit 1 to the camera head 3, and to transmit electronic images and the like from camera head 3 to the control unit 1. The method of communication can be by any of the known wireless techniques which are available, such as those involving infrared, radio, or optical frequencies as disclosed in U.S. Pat. Nos. 4,633,304; 5,027,433; 4,977,618; 4,975,926; and 4,349,014, each of which is hereby fully incorporated by reference herein as those set forth in full.

It should be appreciated, however, that a unidirectional wireless interface is possible in which information is communicated in only one direction, e.g., from the camera head to the control unit. In this case, depending on the direction of the communication, one of transceivers 201 and 210 could be configured simply as a transmitter, and the other of transceivers 201 and 210 could be configured as a receiver. More details on this unidirectional wireless interface will be described later in this disclosure.

A light source 204 and associated light guide 102 provide illumination to the work site. The light guide 102 is used to transmit light from light source 204 to a distal end 103 of endoscope 7. Upon emerging from the distal end 103 of the endoscope, the light is used to illuminate the work site at which the distal tip 103 is situated when in operation. The light guide 102 comprises two portions, portion 211 and portion 212. Portion 212 optically couples light from the light source 204 to the camera head 3. Portion 211 functions to convey a portion of this light from the camera head along the shaft of the endoscope, from the proximal end 101 to the distal tip 103. It is typically constructed from an optical fiber bundle or a liquid light guide extending along the shaft of the endoscope.

A splitter 209 is provided to divert a portion of the light energy from light source 204 as it travels through the light guide 102. The diverted portion of light energy is provided to local power supply 202 which converts the same to electrical energy by means of converter 208. This electrical energy is then used to power the camera head 3 and the components thereof, including imager 32, imager electronics 32a, and transceiver 201.

Advantageously, light guide 102 can be any suitable means for transmitting optical energy, including a bundle of plastic or glass optical fibers, or a liquid light guide. Moreover, splitter 209 can be any suitable means for diverting a portion of the light energy transmitted through the light guide.

In the case in which the light guide 102 comprises a bundle of plastic or glass optical fibers, the splitting function can be accomplished simply by "peeling" away some of the individual fibers in the bundle and positioning them so that they are in operative engagement with the other elements in the power supply, such as the converter. According to this arrangement, the number of fibers which are "peeled" off is in direct proportion with the portion of optical energy which is segregated. For example, in the event it is desired to segregate 20% of the light transmitting through light guide 102, 20% of the fibers in the bundle would be "peeled" away.

Alternatively, the splitter can comprise a partially transmissive and partially reflective mirror placed in the path of light guide 102. A portion of the incident light would be reflected, and an optical coupler could be provided to direct this light to the other elements of the power supply, such as the converter. The remaining portion of the incident light would continue to perform the function of illuminating the work site. According to this arrangement, the portion of light which is segregated would be determined by the relative indices of reflection and transmission of the mirror.

Figure 2:
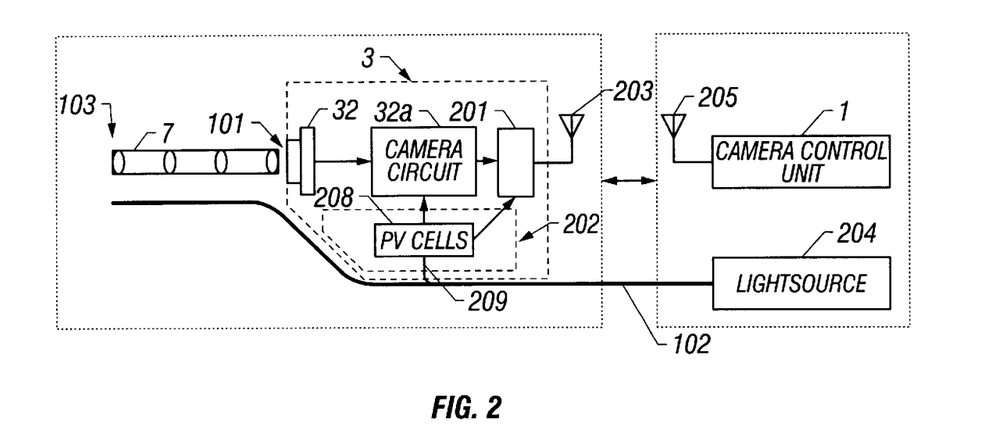
FIG. 2 is a block diagram of a system incorporating a second embodiment of the subject invention.

FIG. 2 illustrates a second embodiment of the subject invention, in which, compared to FIG. 1, like elements are referred to with like identifying numerals. According to this embodiment, splitter 209 comprises at least one fiber peeled away from optical fiber bundle 102.

In this example, the conversion of optical energy to electrical energy is achieved by means of a plurality a photo voltaic ("PV") cells 208. The electrical energy produced by these PV cells is used to power the camera head 3 and the components thereof.

The portion of optical energy which is diverted by the splitter is directed to these cells through a suitable interface. Since PV cells such as these have a non-linear response, and become saturated if over-exposed, it is important to distribute the incident light approximately uniformly over the plurality of cells in order to achieve an efficient conversion into electrical energy. In the case in which the splitter comprises several fibers "peeled" off from the bundle 102, the appropriate distribution of light can be easily achieved by simply arranging the fibers in this "peeled" away portion so that they are distributed relatively uniformly over the cells.

The number of PV cells determines the voltage that can be generated. In the typical case in which about 5 volts are required to drive the camera head, and each cell is capable of providing about 0.7 volts, about 7 PV cells would be required. It should be appreciated, however, that this number can vary depending on the characteristics of the individual cells, and the required voltage.

Moreover, the area over which the cells are arranged determines the power that is generated. For example, in the case in which about 270 mW are required for the camera circuits, and about 230 mW for the wireless transmitter, about 0.5 W must be provided by the PV cells. Assuming a 25% cell efficiency, about 2 watts of light must be applied to the PV cells to generate the required 0.5 watts. Assuming that the PV cells may be illuminated with an intensity of 2000 watts per square meter, the required area over which the cells should be arranged would be about 10 square centimeters, or an area of about 2 cm.×5 cm.

Again, it should be appreciated that this area can vary depending on the required power, the efficiency of the cells, and the intensity of the light that can be provided to the cells. For example, crystalline silicon (Si) cells are about 24% efficient, while gallium arsenide (GaAs) crystalline cells are about 25.1% efficient, and GaInP cells are about 30.3% efficient. Depending on which type of cells are selected, then, the required area may vary.

In this embodiment, the frequency band for the wireless interface is advantageously any of the frequency bands described by CFR 47, vol. 1, section 15.249, including 902–928 MHz, 2400–2483.5 MHz, 5725–5875 MHz, or 24.0–24.56 GHz. The 2400 MHz band, however, is particularly advantageous for use in this embodiment based on known interference possibilities and component costs. Moreover, the modulation technique is advantageously frequency modulation, but it should be appreciated that other modulation techniques, such as amplitude modulation or phase modulation, are possible.

Advantageously, the interface is equipped to allow for a variable carrier frequency, i.e., a frequency which is changeable by the user, or at least the manufacturer's representative, to avoid interference with similar units that may be in use near by. As is common in cordless phones, this frequency selection process could also advantageously be performed automatically at the time the unit is turned on.

Figure 3:
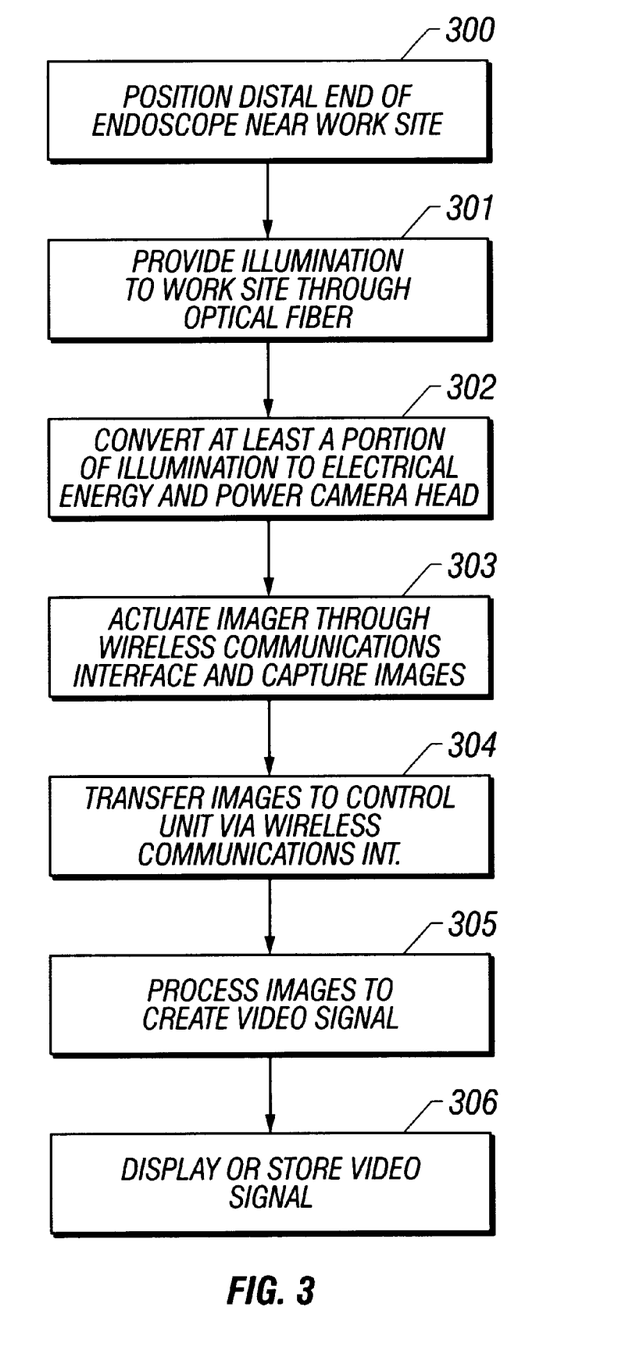
FIG. 3 is a flow diagram illustrating the operation of a system incorporating the first embodiment of the subject invention.

FIG. 3 is a flow diagram of the steps involved in operating a video endoscopic system configured in accordance with the first embodiment of the subject invention.

In step 300, the distal end 103 of the endoscope 7 is positioned near the work site, and in step 301, illumination from light source 204 is provided to the work site by means of light guide 102.

In step 302, a portion of the illumination transmitted through light guide 102 is split off from the main portion by means of splitter 209 and converted to electrical energy by means of converter 208. This electrical energy is then used to power the camera head 3 and the components thereof.

In step 303, control unit 1 actuates imager 32 by transmitting control and synchronization information through the wireless interface formed by transceivers 201 and 210, and antennas 203 and 209. Upon being actuated, the imager captures and provides electronic images responsive to the control and synchronization information provided by control unit 1.

In step 304, the electronic images are transferred to control unit 1 by means of the wireless interface, and in step 305, the electronic images are processed by the control unit, e.g., to form a video signal for displaying on a monitor.

Finally, in step 306, the images are either displayed, stored, or further transmitted.

Figure 4:
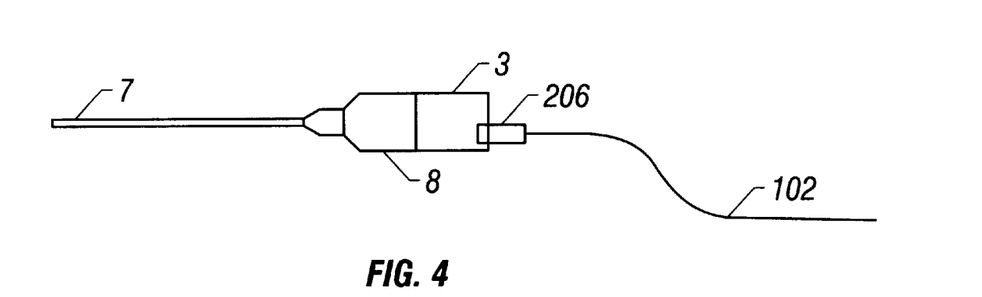
FIG. 4 is a diagram illustrating a third embodiment of the subject invention.

FIG. 4 illustrates a third embodiment of the subject invention in which camera head 3 is directly interfaced to endoscope 7 by means of coupler 8. In this embodiment, light guide 102 is attached to the back of the camera head enclosure by means of connector 206, which is advantageously an easy sealable light interface connector. The light guide extends into the enclosure and then along the endoscope whence it forms a continuous optical path from the light source to the distal tip of the endoscope. As before, it functions to provide illumination to the work site. Meanwhile, splitter 209 splits off a portion of this illumination, and converter 208 converts this split off portion into electrical energy for powering the camera head 3.

Advantageously, light cable input connector 206 is of the type in which the optical face thereof need only be abutted against an adjacent optical window to achieve optical mating therebetween. One example of such a connector is known optical connectors having a metal outside, and a center comprised of either solid glass or a bundle of glass or plastic fibers embedded in epoxy or the like.

Figure 5:
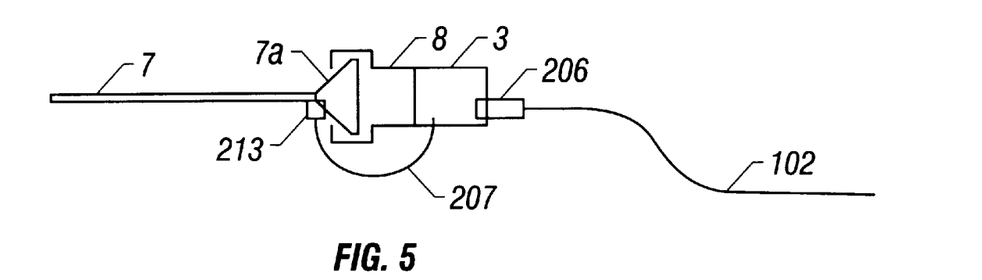
FIG. 5 is a diagram illustrating a fourth embodiment of the subject invention.

FIG. 5 illustrates a fourth embodiment of the subject invention in which the camera head 3 is coupled to eyepiece 7a of endoscope 7 by means of coupler 8. In this embodiment, light guide 102 is again attached to the back of the camera head enclosure by means of connector 206, and a short segment thereof, identified with numeral 207, connects to the usual endoscope light input port 213. Thus, again, a continuous optical path is formed from the light source to the distal tip of the endoscope.

Figure 6:
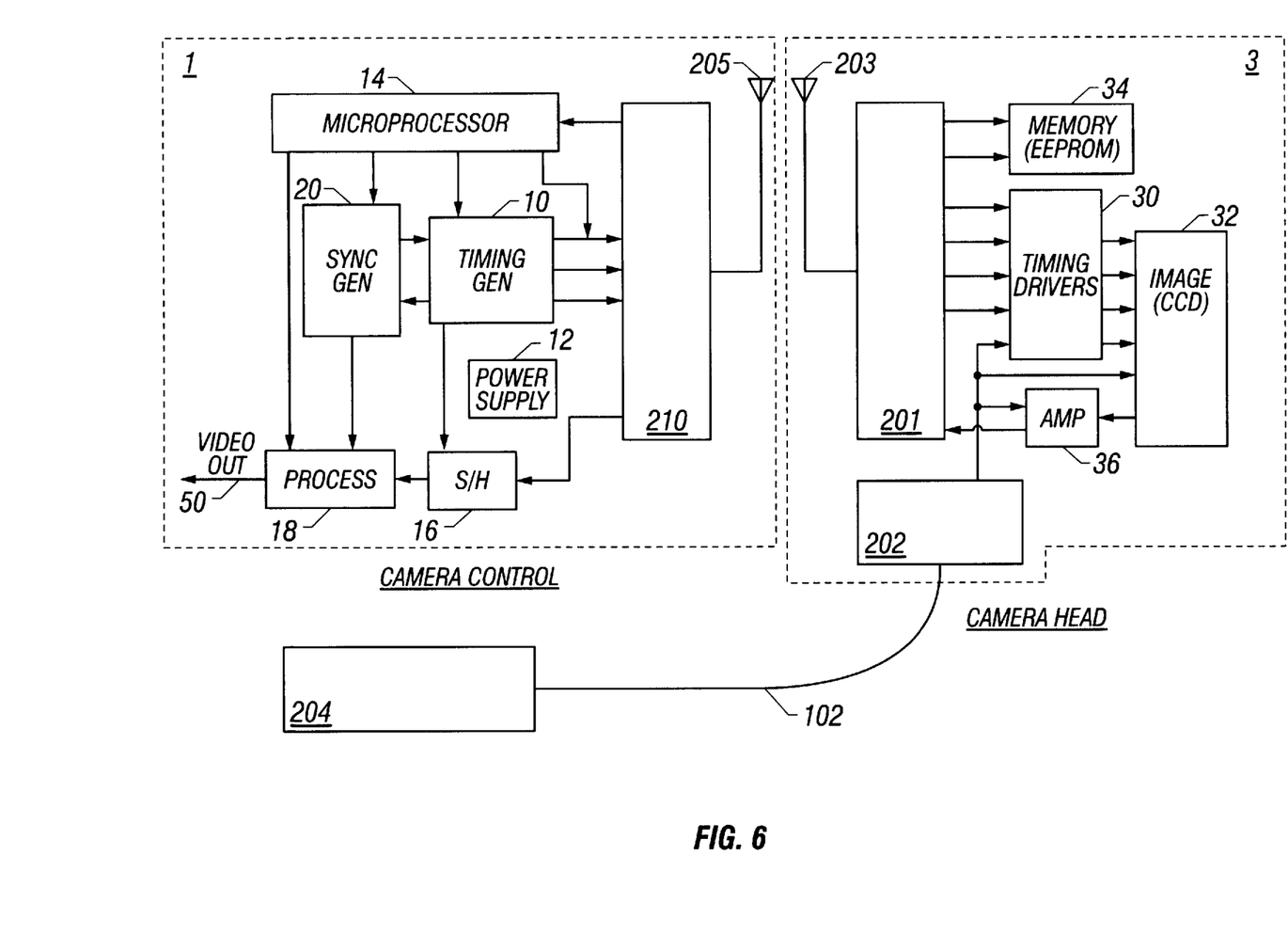
FIG. 6 is a detailed block diagram of a camera head and control circuitry which incorporates a fifth embodiment of the subject invention.

Referring to FIG. 6, a fifth embodiment of a system incorporating the subject invention is illustrated. As shown, the camera control unit 1 includes timing signal generator 10, power supply 12, processing means such as a microprocessor 14, sample and hold circuitry 16, processing circuitry 18, and sync generator 20. A light source provides optical energy to camera head 3 by means of light guide 102. Although this light source is shown in FIG. 6 as being separate from control unit 1, it should be appreciated that embodiments are possible in which the control unit is contained within control unit 1.

Camera control unit 1 also includes transceiver 210 and antenna 205 which, as disclosed, are components of the wireless interface. The camera head unit 3 includes timing driver circuitry 30, a solid state image sensor 32 ("imager"), non-volatile memory device 34 and amplifier 36. Also provided is transceiver 201 and antenna 203 which, as discussed, are components of the wireless interface. A local power supply 202 is also provided to provide power to the camera head. As discussed, this local supply comprises splitter 209 and converter 208. Advantageously, camera head 3 is small for easy manipulation by a physician in a medical procedure, or for observation of industrial processes providing limited space for the camera head.

Timing generator 10 generates timing signals which are sent to the timing driver circuitry 30 via the wireless communications interface. Responsive to the timing signals, timing circuitry 30 generates driving signals which are then provided to the imager 32. Responsive to these driving signals, the imager 32 generates a pre-video signal which is amplified by amplifier 36 and then passed to sample and hold (S/H) circuitry 16 by means of the wireless interface. Responsive to this pre-video signal, the S/H circuitry 16 and the processing circuitry 18 generate a video out signal on line 50 which is sent to other electronics or to video monitor 9 for display. Additional detail regarding the operation and function of these timing and driving signals is found in U.S. Pat. No. 5,696,553 and co-pending U.S. Ser. No. 08/589,875, previously incorporated herein by reference.

Microprocessor 14 communicates by means of the wireless interface to the memory device 34 through a serial clock line and serial data line. Additional detail regarding the operation and function of this microprocessor and memory is available in co-pending U.S. Ser. No. 08/589,875, cited above.

Those skilled in the art will recognize that different components and arrangements thereof may be used in addition to and/or in lieu of those shown in the control unit 1 and camera head 3 of FIG. 6. For example, it should be appreciated that there are several ways to divide functionality between the camera head and the control unit. According to one approach, the following signals would be transmitted over the wireless interface from the control unit to the camera head: pixel clock, horizontal clock, vertical clock, and electronic shutter pulse. From these, the H1, H2, PG, Vsub, shutter, and V1, V2, V3, V4 signals, each of which is known and need not be explained further, would be derived and applied to the imager. Responsive to these signals, the imager would generate a pre-video signal, which would be then passed to the control unit by means of the wireless interface for processing into a video signal.

Advantageously, the imager is one which only requires one voltage, +5V DC. Such an imager is presently available from Sharp Electronics. However, it should be appreciated that other imagers, such as those requiring voltages other than +5V DC, including +15V, −5V, or −9V DC, are also possible. For such imagers, a standard switch mode power converter would be added to create the +15V, −5V, or −9V DC voltages from a single +5V DC source.

According to a second approach, the following signals would be transmitted from the control unit to the camera head: white balance signal and electronic exposure control signal. Responsive to these signals, at least one of the following signals or combination of signals would be generated and then transmitted to the control unit by means of the wireless interface: the pre-video or composite video signals, the luminance and chrominance video signals, or a digital video signal such as Y:U:V sampled as 4:2:2. An explanation of these signals follows:

1. White balance signal: The white balance signal is a known signal used in the white balance process to adjust the red and blue gain values in the camera head 3 so that white objects appear colorless. This permits the camera head to be used with various light sources that have different spectral contents. An arc lamp, for example, has more blue than a quartz lamp; thus, the blue gain must be reduced for white to look white. The process is typically initiated before surgery, by pressing a button on the front panel of the control unit 1, and is performed while the user aims the camera head (with endoscope attached) at a gauze or other white object with the intended light source on.

2. Electronic exposure control signal: This is also a known signal, and is used to adjust the picture brightness. It is typically generated by pressing either an increase or decrease button on the front panel of control unit 1. Once generated, it actuates appropriate circuitry in the camera head 3 to adjust the picture brightness.

3. Luminance/chrominance signals: These are standard video signals, luminance being the brightness component, and chrominance being the color component. Together they carry the full picture information.

4. Digital Video Signal Y:U:V Sampled At 4:2:2: This is a standard digital video signal.

With reference to FIG. 6, the white balance and electronic exposure control signals originate from the microprocessor 14 responsive to the pressing of corresponding buttons on the front panel of control unit 1, while the luminance, chrominance, and digital Y:U:V signals originate from the processing circuitry 18.

According to a third approach, the wireless interface would be unidirectional, and provide only for transmission from the camera head to the control unit. Since the wireless interface would be unidirectional, there would be no need for a transmitter in the control unit or a receiver in the camera head. Thus, element 201 in FIG. 6 need only be a transmitter, and element 210 need only be a receiver. One method of implementing such an approach is to move most if not all of the camera circuitry in the control unit to the camera head, with the camera head sending one or more of the foregoing video or pre-video signals to the control unit, and with the imager being actuated by circuitry within the camera head rather than the control unit.

With reference to FIG. 6, according to this approach, all the elements of block 1 would be moved to the camera head. This is currently feasible because of the recent availability of single chip cameras. The control unit 1 would have a receive, power supply, and part of the process 18 circuit to drive the video. In this approach, it is contemplated that the white balance button used to actuate the white balance process could be located on the camera head.

Figure 7:
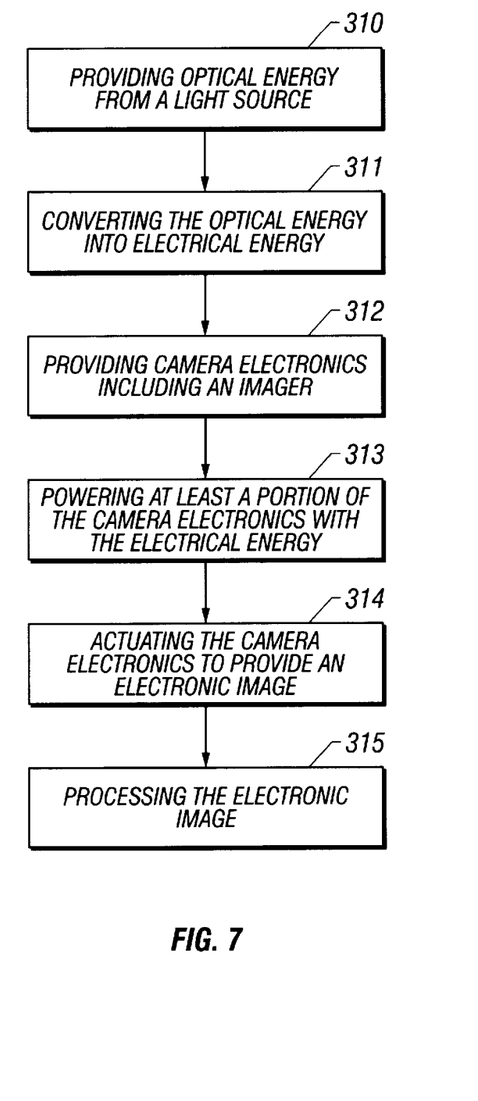
FIG. 7 is a flow diagram illustrating a method of operation of the sixth embodiment of the subject invention.

A sixth embodiment of the subject invention involves a generic video camera system, i.e., a video camera system which is utilized in contexts other than in combination with an endoscope. According to one aspect of this embodiment, the camera head is powered at least in part with electrical energy converted from optical energy obtained from a light source. A method of operation in accordance with this aspect is illustrated in FIG. 7. Step 310 comprises providing optical energy from a light source. Step 311 comprises converting the optical energy into electrical energy. Step 312 comprises providing camera electronics including an imager. Step 313 comprises powering at least a portion of the camera electronics with the electrical energy. Step 314 comprises actuating the camera electronics to produce an electronic image. Step 315 comprises processing the electronic image.

Figure 8:
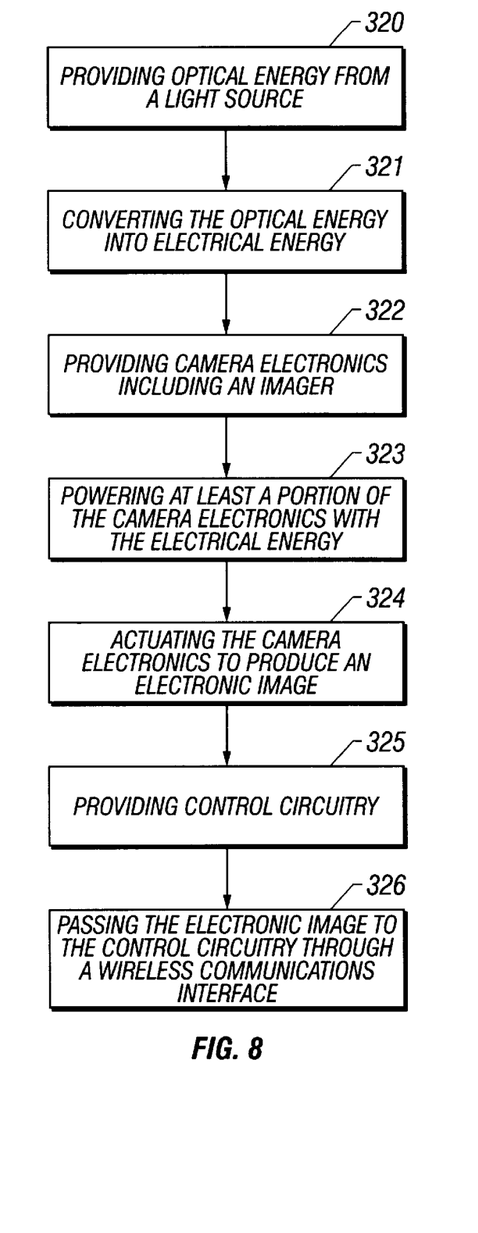
FIG. 8 is a flow diagram illustrating a second method of operation of the sixth embodiment of the subject invention.

According to another aspect of this embodiment, communication between the control unit and the camera head occurs by means of a wireless communications interface. A third aspect involves utilizing the foregoing two aspects in combination. According to this third aspect, communication between the camera head and control unit occurs by means of a wireless communications interface, and the camera head is powered at least in part with electrical energy converted from optical energy provided from a light source. A method of operation in accordance with this third aspect is illustrated in FIG. 8. Step 320 comprises providing optical energy from a light source. Step 321 comprises converting the optical energy into electrical energy. Step 322 comprises providing camera electronics including an imager. Step 323 comprises powering at least a portion of the camera electronics with the electrical energy. Step 324 comprises actuating the camera electronics to produce an electronic image. Step 325 comprises providing control circuity. Step 326 comprises passing the electronic image to the control circuitry through a wireless communications interface.

In light of the foregoing, it can be seen that a video endoscopic system is provided in which the camera head is electrically isolated from the power supply in the control unit. Although a local power supply must now be provided in the camera head, the power which is available and supplied from the same is low enough, that it raises no safety concerns in relation to contact with a patient.

In addition, since light guide 102 is lightweight and flexible, and there is no need for an electrical cable to couple the camera head to the control unit, the ability of a surgeon or other user to easily control and manipulate the camera head endoscope combination is dramatically improved.

Finally, the sterilizability of the system is dramatically improved by the avoidance of an electrical cable and the associated breach in the integrity of the housing of camera head 3 caused by the coupling of such a cable to the camera head. Although light guide 102 must be coupled to the housing of camera head 3, such is readily achieved by an easily sealable light interface connector 206, which optically mates with the camera head without requiring a breach thereof. Accordingly, a substantial enhancement to the sterilizability of the unit is provided.

While embodiments and applications of this invention have been shown and described, it should be apparent to those of ordinary skill in the art that many of the embodiments are possible without departing from the spirit and scope of the subject invention.

Accordingly, the invention is not to be restricted, except as by the appended claims.

We claim:

1. An endoscopic video camera system comprising:

an endoscope;

control circuitry for processing the electronic image as produced by the imager;

a camera head configured for placement along a first optical path extending through the endoscope;

a light source;

a second optical path extending from the light source to the camera head;

the camera head comprising:
camera head electronics including an imager for producing an electronic image; and
a power source for converting at least a portion of the optical energy as transmitted along the second optical path into electrical energy and using the same to power at least part of the camera head electronics, the power source comprising:
a splitter for segregating a portion of the optical energy transmitted along the second optical path; and
a converter for converting the segregated portion of optical energy into electrical energy,
wherein the converter comprises a plurality of photo voltaic cells arranged over an area which is sufficient to deliver necessary power to the camera head electronics given the efficiency of the cells and the intensity of the incident light, and the splitter is configured to allow approximately uniform distribution of light over the cells.

2. The system of claim 1 further comprising a wireless communications interface for allowing wireless communication between the control circuitry and the camera head.

3. The system of claim 2 in which the wireless communications interface is bidirectional.

4. The system of claim 2 in which the wireless communications interface is unidirectional.

5. The system of claim 2 in which the wireless communications interface comprises:

a transceiver and antenna within or coupled to the camera head; and a transceiver and antenna within or coupled to the control circuitry.

6. The system of claim 1 in which the second optical path comprises a bundle of optical fibers and the splitter comprises at least one of these fibers peeled away from the others.

7. The system of claim 1 in which the second optical path is implemented with a liquid light guide.

8. The system of claim 1 in which the light source is located outside a control unit enclosing the control circuitry.

9. The system of claim 1 in which the light source is located within a control unit enclosing the control circuitry.

10. The system of claim 1 in which the imager is a solid state imager.

11. The system of claim 1 in which the imager is a CCD.

12. The system of claim 1 in which the imager is a CMOS imager.

13. The system of claim 1 in which the imager and camera head electronics are configured on a single chip.

14. The system of claim 1 in which the second optical path extends through the endoscope.

15. The system of claim 1 in which the imager produces an electronic image upon being actuated by the control circuitry.

16. An endoscopic video camera system comprising:
an endoscope;
control circuitry for processing an electronic image as produced by the imager;
a camera head configured for placement along a first optical path extending through the endoscope;
a wireless communications interface for allowing wireless communication between the control circuitry and the camera head;
a light source;
a second optical path extending from the light source to the camera head;
the camera head comprising:
camera head electronics including a solid state imager for producing an electronic image; and
a power source for powering at least a portion of the camera electronics comprising:
a splitter for segregating a portion of the optical energy transmitted along the second optical path; and
a converter for converting the segregated portion of optical energy to electrical energy,
wherein the converter comprises a plurality of photo voltaic cells arranged over an area sufficient to deliver necessary power to the camera head electronics given the efficiency of the cells and the intensity of the incident light, and the splitter is configured to allow approximately uniform distribution of light over the cells.

17. The system of claim 16 in which the imager produces an electronic image upon being actuated by the control circuitry.

18. An endoscopic video camera system comprising:
an endoscope;
control circuitry for processing an electronic image as produced by the imager;
a camera head configured for placement along a first optical path extending through the imager;
a bidirectional wireless communications interface for allowing wireless communication between the control circuitry and the camera head comprising:
a transceiver and antenna within or coupled to the camera head; and
a transceiver and antenna within or coupled to the control circuitry;
a light source;
a second optical path implemented with a bundle of optical fibers extending from the light source to the camera head;
the camera head comprising:
camera head electronics including a CMOS imager integrated on a single chip for producing an electronic image; and
a power source for powering at least a portion of the camera electronics comprising:
a splitter comprising at least one optical fiber of the bundle forming the second optical path configured to segregate a portion of the optical energy transmitted along the second optical path and distribute the segregated light approximately uniformly over an area; and
a plurality of photo voltaic cells placed within the area for converting the segregated portion of optical energy into electrical energy,
wherein the area is determined sufficient to deliver necessary power to the camera head electronics given the efficiency of the cells and the intensity of the incident light, and the splitter is configured to allow approximately uniform distribution of light over the cells.

19. The system of claim 18 in which the imager produces an electronic image upon being actuated by the control circuitry.

20. A method of operating an endoscopic video camera system comprising:
positioning an endoscope having a distal end so that the distal end is in proximity with a work site;
illuminating the work site through optical energy provided from a light source;
actuating camera electronics including an imager to produce an electronic image of a target at the work site;
segregating at least a portion of the optical energy provided from the light source;
converting the segregated portion of optical energy into electrical energy using a plurality of photocells arranged over an area determined sufficient to deliver necessary power to the camera head electronics given the efficiency of the cells and the intensity of the incident light, while having the segregated portion of the optical energy approximately uniformly distributed over the photocells;
powering at least a portion of the camera electronics with the electrical energy; and
processing the electronic image in control circuitry.

21. The method claim 20 further comprising transferring through a wireless communications interface the electronic image to the control circuitry.

22. The method of claim 20 further comprising displaying the image on a monitor.

23. The method of claim 20 further comprising storing the image in a storage device.

24. The method of claim 20 further comprising transmitting the image.

25. A video camera system comprising:
control circuitry for processing the electronic image as produced by the imager;
a camera head configured for placement along a first optical path;
a light source; and
a second optical path extending from the light source to the camera head;
the camera head comprising:
camera head electronics including an imager for producing an electronic image; and
a power source for converting at least a portion of the optical energy as transmitted along the second optical path into electrical energy and using the same to power at least part of the camera head electronics, the power source comprising:
a splitter for segregating at least a portion of the optical energy transmitted along the second optical path; and
a converter for converting the segregated portion of optical energy into electrical energy,
wherein the converter comprises a plurality of photo voltaic cells arranged over an area determined sufficient to deliver necessary power to the camera head electronics given the efficiency of the cells and the intensity of the incident light, and the splitter is configured to allow approximately uniform distribution of light over the cells.

26. The system of claim 25 further comprising a wireless communications interface for allowing wireless communication between the control circuitry and the camera head.

27. The system of claim 25 further comprising an endoscope wherein the first optical path extends through the endoscope.

28. A method of operating a video camera system comprising:

provizing optical energy from a light source;

converting said optical energy into electrical energy using a plurality of photocells arranged over an area determined sufficient to deliver necessary power to camera electronics given the efficiency of the cells and the intensity of the incident light, while having at least of portion of said optical energy approximately uniformly distributed over the plurality of photocells;

providing camera electronics including an imager; powering at least a portion of the camera electronics with the electrical energy; actuating the camera electronics to produce an electronic image; and processing the electronic image.

29. The method of claim 28 further comprising passing the electronic image to control circuitry through a wireless communications interface.

30. A method of reducing electromagnetic interference in a video camera system comprising:

providing optical energy from a light source;

converting said optical energy into electrical energy using a plurality of photocells arranged over an area determined sufficient to deliver necessary power to camera electronics given the efficiency of the cells and the intensity of the incident light, while having at least a portion of said optical energy substantially uniformly distributed over the plurality of photocells;

providing camera electronics including an imager;

powering at least a portion of the camera electronics with the electrical energy;

actuating the camera electronics to produce an electronic image;

providing control circuitry; and passing the electronic image to the control circuitry through a wireless communication interface.

* * * * *